(12) United States Patent
Uhrich

(10) Patent No.: US 8,241,668 B2
(45) Date of Patent: *Aug. 14, 2012

(54) THERAPEUTIC POLYESTERS AND POLYAMIDES

(75) Inventor: Kathryn E. Uhrich, Hoboken, NJ (US)

(73) Assignee: Rutgers, the State University of New Jersey, New Brunswick, NJ (US)

( * ) Notice: Subject to any disclaimer, the term of this patent is extended or adjusted under 35 U.S.C. 154(b) by 1089 days.

This patent is subject to a terminal disclaimer.

(21) Appl. No.: 11/956,202

(22) Filed: Dec. 13, 2007

(65) Prior Publication Data

US 2008/0233078 A1 Sep. 25, 2008

Related U.S. Application Data

(60) Continuation of application No. 10/753,048, filed on Jan. 6, 2004, now abandoned, which is a division of application No. 09/917,194, filed on Jul. 27, 2001, now Pat. No. 6,689,350.

(60) Provisional application No. 60/220,707, filed on Jul. 27, 2000, provisional application No. 60/261,337, filed on Jan. 12, 2001.

(51) Int. Cl.
*A61K 9/14* (2006.01)

(52) U.S. Cl. .......................... 424/484; 424/486; 424/78.17

(58) Field of Classification Search ................... 424/484
See application file for complete search history.

(56) References Cited

U.S. PATENT DOCUMENTS

| | | | |
|---|---|---|---|
| 4,062,855 A | 12/1977 | Allan et al. | |
| 4,126,445 A | 11/1978 | Allan et al. | |
| 4,684,620 A | 8/1987 | Hruby et al. | |
| 4,757,128 A | 7/1988 | Domb et al. | |
| 4,792,598 A | 12/1988 | Ziegast | |
| 4,857,311 A | 8/1989 | Domb et al. | |
| 4,868,274 A | 9/1989 | Gupta et al. | |
| 4,886,870 A | 12/1989 | D'Amore et al. | |
| 4,888,176 A | 12/1989 | Langer et al. | |
| 4,891,225 A | 1/1990 | Langer et al. | |
| 4,906,474 A | 3/1990 | Langer et al. | |
| 4,997,904 A | 3/1991 | Domb | |
| 4,999,417 A | 3/1991 | Domb | |
| 5,082,925 A | 1/1992 | Shalaby et al. | |
| 5,175,235 A | 12/1992 | Domb et al. | |
| 5,259,968 A | 11/1993 | Emert et al. | |
| 5,264,540 A | 11/1993 | Cooper et al. | |
| 5,498,729 A | 3/1996 | Domb | |
| 5,514,764 A | 5/1996 | Frechet et al. | |
| 5,518,730 A | 5/1996 | Fuisz | |
| 5,545,409 A | 8/1996 | Laurencin et al. | |
| 5,629,009 A | 5/1997 | Laurencin et al. | |
| 5,902,599 A | 5/1999 | Anseth et al. | |
| 5,916,585 A | 6/1999 | Cook et al. | |
| 5,942,252 A | 8/1999 | Tice et al. | |
| 6,071,530 A | 6/2000 | Polson et al. | |
| 6,153,212 A | 11/2000 | Mao et al. | |
| 6,468,519 B1 | 10/2002 | Uhrich | |
| 6,486,214 B1 | 11/2002 | Uhrich | |
| 6,602,915 B2 | 8/2003 | Uhrich | |
| 6,613,807 B2 | 9/2003 | Uhrich | |
| 6,685,928 B2 | 2/2004 | Uhrich et al. | |
| 6,689,350 B2 | 2/2004 | Uhrich | |
| 7,122,615 B1 | 10/2006 | Uhrich | |
| 7,396,527 B2 | 7/2008 | Uhrich | |
| 7,411,031 B2 | 8/2008 | Uhrich et al. | |
| 7,534,852 B2 | 5/2009 | Uhrich | |
| 7,662,864 B2 | 2/2010 | Kanamathareddy et al. | |
| 7,666,398 B2 | 2/2010 | Uhrich | |
| 2004/0038948 A1 | 2/2004 | Uhrich | |
| 2004/0096476 A1 | 5/2004 | Uhrich et al. | |
| 2005/0249697 A1 | 11/2005 | Uhrich et al. | |
| 2006/0013851 A1 | 1/2006 | Giroux | |
| 2006/0057179 A1 | 3/2006 | Giroux | |
| 2006/0188546 A1 | 8/2006 | Giroux | |
| 2007/0014832 A1 | 1/2007 | Uhrich | |
| 2007/0098800 A1 | 5/2007 | Giroux et al. | |
| 2007/0196417 A1 | 8/2007 | Uhrich | |
| 2008/0226583 A1 | 9/2008 | Uhrich | |
| 2009/0035248 A1 | 2/2009 | Uhrich et al. | |
| 2010/0074937 A1 | 3/2010 | Uhrich | |
| 2010/0152410 A1 | 6/2010 | East et al. | |

FOREIGN PATENT DOCUMENTS

| | | |
|---|---|---|
| DE | 288311 | 3/1991 |
| DE | 288387 | 3/1991 |
| EP | 0246341 | 11/1987 |
| EP | 0483429 | 5/1992 |
| NL | 9000237 | 8/1991 |
| WO | WO-91/09831 | 7/1991 |
| WO | WO-97/39738 | 10/1997 |
| WO | WO-98/36013 | 8/1998 |
| WO | WO-99/12990 | 3/1999 |
| WO | WO-99/29885 | 6/1999 |
| WO | WO-01/28492 | 4/2001 |
| WO | WO 01/41753 | 6/2001 |

(Continued)

OTHER PUBLICATIONS

Dugaiczyk, A., et al., "Nucleotide sequence and the encoded amino acids of human serum albumin mRNA", *Proc. Natl. Acad. Sci.*, USA, 79, 71-75 and 2124, XP009014860, (1982). The Merck Index, Twelfth Edition, Merck & Co., Inc., Ed. By S. Budavari et al., p. 1090, compound 6435, (1996).

Patent Cooperation Treaty, International Search Report of the International Search Authority, PCT/US01/023747, Aug. 21, 2002, 9 pages.

Patent Cooperation Treaty, Written Opinion of the International Search Authority, PCT/US01/023747, Oct. 31, 2002, 2 pages.

Anastasiou, T.J., "Novel Polyanhydrides with Enhanced Thermal and Solubility Properties", *Macromolecules*, 33 (17), 2000, pp. 6217-6221.

Anastasiou, T.J., "Novel, Degradable Polyanhydrides", *25th Annual Meeting Transactions of the Society for Biomaterials*, Abstract, 1999, p. 79

(Continued)

*Primary Examiner* — James Rogers
(74) *Attorney, Agent, or Firm* — Viksnins Harris & Padys PLLP

(57) ABSTRACT

Polymers (i.e. polyesters, polyamides, and polythioesters or a mixture thereof) which degrade hydrolytically into biologically active compounds are provided. Methods of producing these polymers, intermediates useful for preparing these polymers, and methods of using these polymers to deliver biologically active compounds to a host are also provided.

17 Claims, No Drawings

FOREIGN PATENT DOCUMENTS

| | | |
|---|---|---|
| WO | WO-02/09767 | 2/2002 |
| WO | WO-02/09768 | 2/2002 |
| WO | WO-02/09769 | 2/2002 |
| WO | WO 03/046034 | 6/2003 |
| WO | WO 03/065928 | 8/2003 |
| WO | WO 03/066053 | 8/2003 |
| WO | WO 03/072020 | 9/2003 |
| WO | WO 2004/006863 | 1/2004 |
| WO | WO 2004/039355 | 5/2004 |
| WO | WO 2004/045549 | 6/2004 |
| WO | WO 2005/039489 | 5/2005 |
| WO | WO 2005/042600 | 5/2005 |
| WO | WO 2006/127667 | 11/2006 |
| WO | WO 2007/143698 | 12/2007 |
| WO | WO 2008/034019 | 3/2008 |
| WO | WO 2008/103744 | 8/2008 |
| WO | WO 2008/128193 | 10/2008 |
| WO | WO 2009/026544 | 2/2009 |

OTHER PUBLICATIONS

Anastasiou, T.J., "Synthesis of Novel, Degradable Polyanhydrides Containing Para-Aminosalicylic Acid as Drug Delivery Devices for Tuberculosis Treatment", *Polymer Preprints*, 41 (2), (2000), pp. 1366-1367.

Anastasiou, T.,et al. ,"Synthesis of Novel , Degradable Polyanhydrides Containing Para-Aminosalicylic Acid as Drug Delivery Devices for Tuberculosis Treatment", *Polymer Preprints*, 41(2), (2000),p. 1366.

Attawia, M.A., "Biocompatibility Testing of Poly(anhydride-co-imides) Containing Pyromellitylimidoalanine", *The 21st Annual Meeting of the Society for Biomaterials*, Abstract,(1994), p. 222.

Attawia, M.A., "Cytotoxicity testing of poly(anhydride-co-imides) for orthopedic applications", *Journal of Biomedical Materials Research*, 29, (1995),pp. 1233-1240.

Attawia, M.A., "In Vitro Bone Biocompatibility of Poly(anhydride-co-imides) Containing Pyromellitylimidoalanine", *Journal of Orthopedic Research*, 14 , (1996), pp. 445-454.

Attawia, M.A., "Proliferation, Morphology, and Protein Expression by Osteoblasts Cultured on Poly(anhydride-co-amides)", *J. Biomed. Mater. Res. (Appl. Biomater)*, 48, (1999), pp. 322-327.

Attawia, M.A., "Regional drug delivery with radiation for the treatment Ewing's sarcoma—In vitro development of a taxol release system", *Journal of Controlled Release*, 71, (2001), pp. 193-202.

Attawia, M.A., "The Long Term Osteoblast Response to Poly(anhydride-co-imides): A New Degradable Polymer for Use in Bone", *Proc. of the Fifth World Biomaterials Congress*, Toronto, Canada (1996), p. 113.

Beaton, M.L., "Synthesis of a novel poly(anhydride-ester)", *The Rutgers Scholar—An Electronic Bulletin of Undergraduate Research*, 3, www.rutgersscholar.rutgers.edu/volume03/beatuhri/beatuhri.html, (2001), 7 pgs.

Bedell, C., "Processing and Hydrolytic Degradation of Aromatic, Ortho-Substituted Polyanhydrides", *Journal of Applied Polymer Science*, 80, (2001), pp. 32-38.

Campo, C.J., "Polyanhydrides: the effects of ring substitution changes on polymer properties", *Polymer Bulletin*, 42, (1999), pp. 61-68.

Chafi, N..,"Dosage Form with Salicylic Acid Attached to the Polyanhydride Polymer Dispersed in an Eudragit Matrix", *International Journal of Pharmaceutics*, 52, (1989), pp. 203-211.

Chatterjee, R.,et al. ,"Mechanism for the Increase in Solubility to Deoxyhemoglobin S Due to Cross-Linking the beta Chains between Lysine-82beta1 and Lysine-82-beta2", *Biochemistry*, 21, (1982),5901-5909.

Conix, A..,"Aromatic Polyanhydrides, a New Class of High Melting Fiber-Forming Polymers", *Journal of Polymer Science*, XXIX, (1958),pp. 343-353.

Conix, A..,"New High-Melting Fibre-Forming Polymers", *Die Makromolekulare Chemie*, XXIV, (1957),pp. 76-78.

Conix, A..,"Poly[1,3-bis(p-carboxyphenoxy)-Propane anhydride]", *Macromolecular Synthesis*, 2, (1996), pp. 95-99.

Davaran, S.,et al. ,"Release of 5-amino Salicylic Acid from Acrylic Type Polymeric Prodrugs Designed for Colon-specific Drug Delivery", *Journal of Controlled Release*, 58, (1999),279-287.

Domb, A.J., "Synthesis and Characterization of Biodegradable Aromatic Anhydride Copolymers", *Macromolecules*, 25, (1992), pp. 12-17.

Dukovic, G., "Novel degradable poly(anhydride-esters) for controlled drug release", *The Rutgers Scholar—An Electronic Bulletin of Undergraduate Research*, 1, http://rutgersscholar.rutgers.edu/colume01/uhriduko/uhriduko.html, (1999), 10 pgs.

Erdman, L..,et al., "Polymer Prodrugs with Pharmaceutically Active Degradation Products", *Polymer Preprints*, 38 (2), (1997), pp. 570-571.

Erdmann, L.,et al. ,"Polymer Prodrugs with Pharmaceutically Active Degradation Products", *Proceedings of the 1997 American Chemical Society Las Vegas Meeting*, Las Vegas, NV, (Sep. 7-12, 1997),p. 570-571.

Erdmann, L., "Chapter 5: Polymeric Prodrugs: Novel Polymers with Bioactive Components", In: *Tailored Polymeric Materials for Controlled Delivery Systems*, I. McCulloch, et al., (Editors), ACS Symposium Series 709, American Chemical Society: Washington, D.C., (1998), pp. 83-91.

Erdmann, L.,et al. ,"Polymeric Prodrugs: Novel Polymers with Bioactive Components", *American Chemical Society*, (1993),pp. 83-91.

Erdmann, L., "Degradable poly(anhydride ester) implants: effects of localized salicylic acid release on bone", *Biomaterials*, 21, (2000), pp. 2507-2512.

Erdmann, L., "Polymeric Prodrugs: Novel Polymers for Delivery of Salicylic Acid", *Annals of Biomedical Engineering*, 26, (Suppl. 1), Abstract No. PB.26, Annual Fall Meeting, (1998), p. S-124.

Erdmann, L., "Polymeric Salicylic Acid: In Vitro and In Vivo Degradation", *Polymer Preprints*, 39, (2), (1998), p. 224-225.

Erdmann, L., "Synthesis and Characterization of a Polymeric Prodrug", *Proceedings of the American Chemical Society Division of Polymeric Materials: Science and Enginneering*, 78, Abstract of Spring Meeting, Dallas, TX, (1998),p. 194.

Erdmann, L..,"Synthesis and degradation characteristics of salicylic acid-derived poly(anhydrid-esters)", *Biomaterials*, 21, (2000), pp. 1941-1946.

Giammona, G., "Polymeric Prodrugs alpha beta poly-hyroxyethyl-d1-aspartamide as macromolecular carrier for some non-steroidal anti-inflammatory agents", *Abstract from Database BIOSIS Online, Biosciences Information Service*, Philadelphia, PA, Original Publication from the International Journal of Pharmaceutics (Amsterdam), (1989), 1 pg.

Gouin, S..,et al., "New Polyanhydrides Made from a Bile Acid Dimer and Sebacic Acid: Synthesis, Characterization, and Degradation", *Macrmolecules*, 33, (2000), pp. 5379-5383.

Ibim, S..,"Controlled Release Based on Poly(anhydride-co-imides)", *Proc. Intern. Symp. Control. Rel. Bioact. Mater.*, 22, (1995),2 pgs.

Ibim, S.M., "Poly(anhydride-co-imides): In Vivo Biocompatibility in a rat model", *Biomaterials*, 19, (1998),pp. 941-951.

Ibim, S.E., "Preliminary In Vivo Report on the Osteocompatibility of Poly(anhydride-co-imides) evaluated in a Tibial Model", *App. Biomater.* 43(4) (1998),pp. 374-379.

Jiang, H.L. ,et al. ,"Synthesis, Characterization and In Vitro Degradation of a New Family of Alternate Poly(ester-anhydrides) Based on Aliphatic and Aromatic Diacids", *Biomaterials*, 22, (2001),211-218.

Krogh-Jespersen, E.,"Synthesis of a Novel Aromatic Polyanhydride Containing Aminosalicylic Acid", *Polymer Preprints*, 41 (1) , (2000),pp. 1048-1049.

Langer, R..,"New Methods of Drug Delivery", *Science* 249, (1990),pp. 1527-1533.

Laurencin, C.T., "Poly(andrides-co-imides): In Vivo Biocompatibility Study", *23rd Annual Meeting of the Society for Biomaterials, Meeting of the Society for Biomaterials*, New Orleans, LA, (1997), p. 483.

Laurencin, C.T., "The Biocompatibility of Poly(anhydride-co-imides): High Strength Polymers for Controlled Drug Delivery", *Proc. 24th Int'l Symp. Control. Rel. Bioact. Mater.*, (1997),pp. 973-974.

Laurencin, C.T., "The Bone Biocompatibility of Poly(anhydride-co-imides)—A new generation degradable Polymer for Orthopedic Applications", *41st Annual Meeting of the Orthopedic Research Society*, Orlando, FL, (1995), pp. 143-224, Laurencin, C.T., "The Controlled Delivery of Radiosensitizers: Taxol Treatment for Ewing Sarcoma", *Proc. of the 25th Int'l Symp. Control. Rel. Bioact. Mater.*, (1998), pp. 236-237.

Macedo, B..,et al., "The in vivo Response to a Bioactive Biodegadable Polymer", *Journal of Dental Research*, 78, Abstract No. 2827, (1999), p. 459.

Macedo, B.,"The In Vivo Response to Bioactive Polyanhydride Monofilament", *Journal of Dental Research*, 79 (Abstract No. 3872), (2000), p. 627.

Pinther, P., "Synthesis of Polyanhydrides Containing Rapid Ester Groups", *Makromol. Chem., Rapid Commun.*, 11, (1990), pp. 403-408

Schacht, E.,et al. ,"Polymers for Colon Specific Delivery",*Journal of Controlled Release*, 39 (1996),327-338.

Seidel, J.O., "Erosion of Poly(anhydride-co-imides): A Preliminany Mechanistic Study", *J. Appl. Polym. Sci.* 62(8) (1996), pp. 1277-1283.

Shen, E.,"Morphological Characterization of Erodible Polymer Carriers for Drug Release", *Proc. 26th Int'l Symp. Control. Rel. Bioact. Mater.*, (1999), pp. 717-718.

Uhrich, K.E., "Chemical Changes during in vivo degradation of poly(anhydride-imide) matrices", *Biomaterials*, 19, (1998),pp. 2045-2050.

Uhrich, K.E., "Degradation of poly(anhydride-co-imides): Novel Polymers for Orthopedic Applications", *Mat. Res. Soc. Symp. Proc.*, 394 , (1995), pp. 41-46.

Uhrich, K.E., "In Vitro Degradation Characteristics of Poly(anhydride-imides) Containing Pyromellitylimidoalanine", *J. Appl. Polymer Sci., Part A, Polym. Chem.*, 34 (7), (1996), pp. 1261-1269.

Uhrich, K.E., "In Vitro Degradation Characteristics of Poly(anhydride-imides) Containing trimellitylimidoglycine", *J. Appl. Polymer. Sci.*, 63(11), (1997), pp. 1401-1411.

Uhrich, K.E., "Poly(anhydride-ester) Degradation: Mechanical Changes and Correlation to Antibiotic Release", *American Chemical Society, Abstracts of Papers, Part 2*, Abstract No. 121, 2221st ACS National Meeting, San Diego, CA,(2001), 1 pg.

Uhrich, K.E., "Synthesis and Characterization of Degradable poly(anhydride-co-imides)", *Macromolecules*, 28 (7), (1995), pp. 2184-2193.

Uhrich, K.E., "Synthesis and Characterization of poly(anhydride-co-imides): Solution Polycondensation of Biodegradable Polymers Derived from Amino Acids", *Proc. of the American Chemical Society, Division of Polymers Materials: Science and Engineerings*, 70, Spring Meeting, San Diego, CA, (1994), pp. 239-240.

Uhrich, K.E., "Synthesis of Aminosalicylate-based polyanhydride Prodrugs: Esters, Amides, and Azos", *American Chemical Society, Abstracts of Papers, Part 2*, Abstract No. 407, 222nd ACS National Meeting, Chicago, IL,(2001),1 pg.

Yazdi, M., et al., "Effects of non-steroidal anti-inflammatory drugs on demineralized bone-induced bone formation", *Journal of Periodontal Research*, 27 (1) (1992), pp. 28-33.

Woo, G.L.Y., et al., "Synthesis and characterization of a novel biodegradable anitmicrobial polymer", *Biomaterial*, 21, 1235-1246, (2000).

THERAPEUTIC POLYESTERS AND POLYAMIDES

PRIORITY OF INVENTION

This application is a continuation of U.S. patent application Ser. No. 10/753,048, filed 6 Jan. 2004 now abandoned, which is a divisional application of U.S. patent application Ser. No. 09/917,194, filed 27 Jul. 2001, now U.S. Pat. No. 6,689,350; this application also claims priority from U.S. Provisional Application No. 60/220,707, filed 27 Jul. 2000 and U.S. Provisional Application No. 60/261,337, filed 12 Jan. 2001.

BACKGROUND OF THE INVENTION

Polyesters are used routinely by those skilled in the art in various drug delivery systems.

For example, U.S. Pat. No. 5,942,252 describes a microcapsule comprising as its biocompatible excipient a poly(lactide-co-glycolide), poly(lactide), poly(glycolide), copolyoxalate, polycaprolactone, poly(lactide-co-caprolactone), poly(esteramide), polyorthoester, poly(p-hydroxybutyric) acid and/or polyanhydride for use in delivering antigens or vaccines into and through mucosally-associated lymphoid tissue.

WO 99/29885 describes a process for degrading poly(ester-amides) and poly(ester-urethanes) encapsulating chemicals, drugs, enzymes, microorganisms and seeds by introducing the polymer to an aqueous nutrient solution and inoculating the solution with a culture containing a selected bacteria.

WO 98/36013 describes aliphatic-aromatic dihydroxy compounds for use as controlled drug delivery systems.

WO 97/39738 describes preparation of microparticles of a sustained release ionic conjugate comprising a free carboxyl group containing biodegradable polymers and a free amino group-containing drug.

SUMMARY OF THE INVENTION

Polyesters, polythioesters, and polyamides which degrade into useful biologically active compounds have now been developed. Accordingly, the invention provides a polymer of the invention which is polymer comprising a backbone, wherein the backbone comprises ester, thioester, or amide linkages, and wherein the backbone comprises one or more groups that will yield a biologically active compound upon hydrolysis of the polymer.

The invention also provides a pharmaceutical composition comprising a polymer of the invention and a pharmaceutically acceptable carrier.

The invention also provides a therapeutic method for treating a disease in an animal comprising administering to an animal in need of such therapy, an effective amount of a polymer of the invention.

The invention also provides a method of delivering a biologically active compound to a host comprising administering to the host a biocompatible and biodegradable polymer of the invention, which degrades into the biologically active compound.

The invention provides a polymer of the invention for use in medical therapy, as well as the use of a polymer of the invention for the manufacture of a medicament useful for the treatment of a disease in a mammal, such as a human.

The invention also provides processes and intermediates disclosed herein that are useful for preparing a polymer of the invention.

DETAILED DESCRIPTION OF THE INVENTION

Definitions

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1$-$C_6)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

The term ester linkage means —OC(=O)— or —C(=O)O—; the term thioester linkage means —SC(=O)— or —C(=O)S—; and the term amide linkage means —N(R)C(=O)— or —C(=O)N(R)—, wherein each R is a suitable organic radical, such as, for example, hydrogen, $(C_1$-$C_6)$alkyl, $(C_3$-$C_6)$cycloalkyl, $(C_3$-$C_6)$cycloalkyl$(C_1$-$C_6)$alkyl, aryl, heteroaryl, aryl$(C_1$-$C_6)$alkyl, or heteroaryl$(C_1$-$C_6)$alkyl.

The term "amino acid," comprises the residues of the natural amino acids (e.g. Ala, Arg, Asn, Asp, Cys, Glu, Gln, Gly, His, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a $(C_1$-$C_6)$alkyl, phenyl or benzyl ester or amide; or as an α-methylbenzyl amide). Other suitable amino and carboxy protecting groups are known to those skilled in the art (See for example, Greene, T. W.; Wutz, P. G. M. "Protecting Groups In Organic Synthesis" second edition, 1991, New York, John Wiley & sons, Inc., and references cited therein).

The term "host" includes animals and plants.

The term "peptide" describes a sequence of 2 to 35 amino acids (e.g. as defined hereinabove) or peptidyl residues. The sequence may be linear or cyclic. For example, a cyclic peptide can be prepared or may result from the formation of disulfide bridges between two cysteine residues in a sequence. Preferably a peptide comprises 3 to 20, or 5 to 15 amino acids. Peptide derivatives can be prepared as disclosed in U.S. Pat. Nos. 4,612,302; 4,853,371; and 4,684,620, or as described in the Examples hereinbelow. Peptide sequences specifically recited herein are written with the amino terminus on the left and the carboxy terminus on the right.

Polymers of the Invention

The biocompatible, biodegradable polyesters, polythioesters, and polyamides of the invention are useful in a variety of applications where delivery of a biologically active compound is desired. Examples of such applications include, but are not limited to, medical, dental and cosmetic uses.

The polymers of the invention may be prepared in accordance with methods commonly employed in the field of synthetic polymers to produce a variety of useful products with valuable physical and chemical properties. The polymers can be readily processed into pastes or solvent cast to yield films, coatings, microspheres and fibers with different geometric shapes for design of various medical implants, and may also be processed by compression molding and extrusion.

Polyesters and polyamides prepared in accordance with the present invention have average molecular weights of about 1500 Daltons up to about 100,000 Daltons, calculated by Gel Permeation Chromatography (GPC) relative to narrow molecular weight polystyrene standards. Preferred polyesters and polyamides have average molecular weights of about 1500 Daltons, up to about 50,000 Daltons calculated by Gel Permeation Chromatography (GPC) relative to narrow molecular weight polystyrene standards. Preferred polyesters and polyamides have average molecular weights of about 1500 Daltons, up to about 35,000 Daltons.

Medical implant applications include the use of polyesters, polythioesters, or polyamides to form shaped articles such as vascular grafts and stents, bone plates, sutures, implantable sensors, implantable drug delivery devices, stents for tissue regeneration, and other articles that decompose into non-toxic components within a known time period.

Polymers of the present invention can also be incorporated into oral formulations and into products such as skin moisturizers, cleansers, pads, plasters, lotions, creams, gels, ointments, solutions, shampoos, tanning products and lipsticks for topical application.

Although the invention provides homopolymers that are prepared from suitably functionalized biologically active compounds, Applicant has discovered that the mechanical and hydrolytic properties of polymers comprising one or more biologically active compounds can be controlled by incorporating a linking group (L) into the polymer backbone.

Preferably, the polymers of the invention comprise backbones wherein biologically active compounds and linker groups are bonded together through ester linkages, thioester linkages, amide linkages, or a mixture thereof. Due to the presence of the ester, thioester, and/or amide linkages, the polymers can be hydrolyzed under physiological conditions to provide the biologically active compounds. Thus, the polymers of the invention can be particularly useful as a controlled release source for a biologically active compound, or as a medium for the localized delivery of a biologically active compound to a selected site. For example, the polymers of the invention can be used for the localized delivery of a therapeutic agent to a selected site within the body of a human patient (i.e. within or near a tumor), where the degradation of the polymer provides localized, controlled, release of the therapeutic agent.

Biologically Active Compounds

The term "biologically active compound" includes therapeutic agents that provide a therapeutically desirable effect when administered to an animal (e.g. a mammal, such as a human). Biologically active compounds that can be incorporated into the polymers of the invention possess at least two functional groups that can each be incorporated into an ester, thioester, or amide linkage of a polymer (as discussed in detail below), such that, upon hydrolysis of the polymer, the therapeutic agent is obtained. These groups can independently be a hydroxy group (—OH), a mercapto group (—SH), an amine group (—NHR), or a carboxylic acid (—COOH).

The biologically active compounds can also comprise other functional groups (including hydroxy groups, mercapto groups, amine groups, and carboxylic acids, as well as others) that can be used to modify the properties of the polymer (e.g. for branching, for cross linking, for appending other molecules (e.g. another biologically active compound) to the polymer, for changing the solubility of the polymer, or for effecting the biodistribution of the polymer). Lists of therapeutic agents can be found, for example, in: Physicians' Desk Reference, 55 ed., 2001, Medical Economics Company, Inc., Montvale, N.J.; USPN Dictionary of USAN and International Drug Names, 2000, The United States Pharmacopeial Convention, Inc., Rockville, Md.; and The Merck Index, 12 ed., 1996, Merck & Co., Inc., Whitehouse Station, N.J. One skilled in the art can readily select therapeutic agents that possess the necessary functional groups for incorporation into the polymers of the invention from these lists.

Therapeutic agents that can be incorporated into the polymers of the invention include suitably functionalized analgesics or general or local anesthetics, anti-convulsants, anti-diabetic agents, anti-fibrotic agents, anti-infectives, antibacterials, anti-fungals, anti-neoplastics, cardioprotective agents, cardiovascular agents, anti-thrombotics, central nervous system stimulants, cholinesterase inhibitors, contraceptives, deodorants, dopamine receptor agonists, erectile dysfunction agents, fertility agents, gastrointestinal agents, gout agents, hormones, immunomodulators, immunosuppressives, migraine agents, non-steriodal anti-inflammatory drugs (NSAIDs), motion sickness agents, muscle relaxants, nucleoside analogs, neurodegenerative agents (e.g, Parkinson's disease), obesity agents, ophthalmic agents, osteoporosis agents, parasympatholytics, parasympathommetics, anti-anesthetics, prostaglandins, psychotherapeutic agents, respiratory agents, sedatives, hypnotics, skin and mucous membrane agents, smoking sessation agents, sympatholytics, urinary tract agents, vaginal agents, and vasodilators (see Physicians' Desk Reference, 55 ed., 2001, Medical Economics Company, Inc., Montvale, N.J., pages 201-202).

Linking Group "L"

The nature of the linking group "L" in a polymer of the invention is not critical provided the polymer of the invention possesses acceptable mechanical properties and release kinetics for the selected therapeutic application. The linking group L is typically a divalent organic radical having a molecular weight of from about 25 daltons to about 400 daltons. More preferably, L has a molecular weight of from about 40 daltons to about 200 daltons.

The linking group L typically has a length of from about 5 angstroms to about 100 angstroms using standard bond lengths and angles. More preferably, the linking group L has a length of from about 10 angstroms to about 50 angstroms.

The linking group may be biologically inactive, or may itself possess biological activity. The linking group can also comprise other functional groups (including hydroxy groups, mercapto groups, amine groups, carboxylic acids, as well as others) that can be used to modify the properties of the polymer (e.g. for branching, for cross linking, for appending other molecules (e.g. another biologically active compound) to the polymer, for changing the solubility of the polymer, or for effecting the biodistribution of the polymer).

Specific And Preferred Values

Specific and preferred values listed herein for radicals, substituents, groups, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; (C$_3$-C$_6$)cycloalkyl can be cyclopropyl, cyclobutyl, cyclopentyl, or cyclohexyl; (C$_3$-C$_6$)cycloalkyl(C$_1$-C$_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; (C$_1$-C$_6$) alkoxy can be methoxy, ethoxy, propoxy, isopropoxy, butoxy, iso-butoxy, sec-butoxy, pentoxy, 3-pentoxy, or hexyloxy; (C$_1$-C$_6$)alkanoyl can be acetyl, propanoyl or butanoyl; (C$_1$-C$_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; (C$_1$-C$_6$)alkylthio can be methylthio, ethylthio, propylthio, isopropylthio, butylthio, isobutylthio, pentylthio, or hexylthio; (C$_2$-C$_6$)alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazolyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific biologically active compound that can be incorporated into the polymers of the invention is atorvastatin; enalapril; ranitidine; ciprofloxacin; pravastatin; clarithromycin; cyclosporin; famotidine; leuprolide; acyclovir; paclitaxel; azithromycin; lamivudine; budesonide; albuterol; indinavir; metformin; alendronate; nizatidine; zidovudine; carboplatin; metoprolol; amoxicillin; diclofenac; lisinopril; ceftriaxone; captopril; salmeterol; xinafoate; imipenem; cilastatin; benazepril; cefaclor; ceftazidime; morphine; dopamine; bialamicol; fluvastatin; phenamidine; podophyllinic acid 2-ethylhydrazine; acriflavine; chloroazodin; arsphenamine; amicarbilide; aminoquinuride; quinapril; oxymorphone; buprenorphine; butorphanol; nalbuphine. streptozocin; doxorubicin; daunorubicin; plicamycin; idarubicin; mitomycin C; pentostatin; mitoxantrone; cytarabine; fludarabine phosphate; floxuridine; cladribine; 6-mercaptopurine; thioguanine; capecitabine; docetaxel; etoposide; gemcitabine; topotecan; vinorelbine; vincristine; vinblastine; teniposide; melphalan; methotrexate; 2-p-sulfanilyanilinoethanol; 4,4'-sulfinyldianiline; 4-sulfanilamidosalicylic acid; acediasulfone; acetosulfone; amikacin; amphotericin B; ampicillin; apalcillin; apicycline; apramycin; arbekacin; aspoxicillin; azidamfenicol; aztreonam; bacitracin; bambermycin(s); biapenem; brodimoprim; butirosin; capreomycin; carbenicillin; carbomycin; carumonam; cefadroxil; cefamandole; cefatrizine; cefbuperazone; cefclidin; cefdinir; cefditoren; cefepime; cefetamet; cefixime; cefmenoxime; cefminox; cefodizime; cefonicid; cefoperazone; ceforanide; cefotaxime; cefotetan; cefotiam; cefozopran; cefpimizole; cefpiramide; cefpirome; cefprozil; cefroxadine; cefteram; ceftibuten; cefuzonam; cephalexin; cephaloglycin; cephalosporin C; cephradine; chloramphenicol; chlortetracycline; clinafloxacin; clindamycin; clomocycline; colistin; cyclacillin; dapsone; demeclocycline; diathymosulfone; dibekacin; dihydrostreptomycin; dirithromycin; doxycycline; enoxacin; enviomycin; epicillin; erythromycin; flomoxef; fortimicin(s); gentamicin(s); glucosulfone solasulfone; gramicidin S; gramicidin(s); grepafloxacin; guamecycline; hetacillin; isepamicin; josamycin; kanamycin(s); leucomycin(s); lincomycin; lomefloxacin; lucensomycin; lymecycline; meclocycline; meropenem; methacycline; micronomicin; midecamycin(s); minocycline; moxalactam; mupirocin; nadifloxacin; natamycin; neomycin; netilmicin; norfloxacin; oleandomycin; oxytetracycline; p-sulfanilylbenzylamine; panipenem; paromomycin; pazufloxacin; penicillin N; pipacycline; pipemidic acid; polymyxin; primycin; quinacillin; ribostamycin; rifamide; rifampin; rifamycin SV; rifapentine; rifaximin; ristocetin; ritipenem; rokitamycin; rolitetracycline; rosaramycin; roxithromycin; salazosulfadimidine; sancycline; sisomicin; sparfloxacin; spectinomycin; spiramycin; streptomycin; succisulfone; sulfachrysoidine; sulfaloxic acid; sulfamidochrysoidine; sulfanilic acid; sulfoxone; teicoplanin; temafloxacin; temocillin; tetroxoprim; thiamphenicol; thiazolsulfone; thiostrepton; ticarcillin; tigemonam; tobramycin; tosufloxacin; trimethoprim; trospectomycin; trovafloxacin; tuberactinomycin; vancomycin; azaserine; candicidin(s); chlorphenesin; dermostatin(s); filipin; fungichromin; mepartricin; nystatin; oligomycin(s); perimycin A; tubercidin;6-azauridine; 6-diazo-5-oxo-L-norleucine; aclacinomycin(s); ancitabine; anthramycin; azacitadine; azaserine; bleomycin(s); carubicin; carzinophillin A; chlorozotocin; chromomycin(s); denopterin; doxifluridine; edatrexate; eflornithine; elliptinium; enocitabine; epirubicin; mannomustine; menogaril; mitobronitol; mitolactol; mopidamol; mycophenolic acid; nogalamycin; olivomycin(s); peplomycin; pirarubicin; piritrexim; prednimustine; procarbazine; pteropterin; puromycin; ranimustine; streptonigrin; thiamiprine; Tomudex® (N-[[5-[[(1,4-Dihydro-2-methyl-4-oxo-6-quinazolinyl)methyl]methylamino]-2-thienyl]carbonyl]-L-glutamic acid), trimetrexate, tubercidin, ubenimex, vindesine, zorubicin; argatroban; coumetarol; dicoumarol; ethyl biscoumacetate; ethylidene dicoumarol; iloprost; lamifiban; taprostene; tioclomarol; tirofiban; amiprilose; bucillamine; gusperimus; mycophenolic acid; procodazole; romurtide; sirolimus (rapamycin); tacrolimus; butethamine; fenalcomine; hydroxytetracaine; naepaine; orthocaine; piridocaine; salicyl alcohol; 3-amino-4-hydroxybutyric acid; aceclofenac; alminoprofen; amfenac; bromfenac; bromosaligenin; bumadizon; carprofen; diclofenac; diflunisal; ditazol; enfenamic acid; etodolac; etofenamate; fendosal; fepradinol; flufenamic acid; gentisic acid; glucamethacin; glycol salicylate; meclofenamic acid; mefenamic acid; mesalamine; niflumic acid; olsalazine; oxaceprol; S-adenosylmethionine; salicylic acid; salsalate; sulfasalazine; or tolfenamic acid.

A preferred biologically active compound suitable for incorporation into polyesters of the invention is morphine, dopamine, bialamicol, or tetracycline.

A preferred biologically active compound suitable for incorporation into polyamides of the present invention is phenamidine, acriflavine, chloroazodin, arsphenamine, amicarbilide or aminoquinuride.

Another preferred biologically active compound that can be incorporated into a polymer of the invention is oxymorphone, buprenorphine, butorphanol, or nalbuphine.

Another preferred biologically active compound that can be incorporated into a polymer of the invention is methotrexate, doxorubicin, or daunorubicin.

Another preferred biologically active compound that can be incorporated into a polymer of the invention is atorvastatin, enalapril, ranitidine, pravastatin, cyclosporin, famotidine, leuprolide, acyclovir, lamivudine, budesonide, albuterol, indinavir, metformin, alendronate, nizatidine, zidovudine, carboplatin, metoprolol, lisinpril, captopril, salmeterol, cilastatin, benazepril, cefaclor, fluvastatin, quinapril, gemcitabine or vincristine.

Another preferred biologically active compound that can be incorporated into a polymer of the invention is a nonsteroidal anti-inflammatory drug, for example, a nonsteroidal anti-inflammatory drug as described in U.S. patent application (Ser. No. 09/732,516, filed 7 Dec. 2000), 3-amino-4-hydroxybutyric acid, aceclofenac, alminoprofen, amfenac, bromfenac, bromosaligenin, bumadizon, carprofen, diclofenac, diflunisal, ditazol, enfenamic acid, etodolac, etofenamate, fendosal, fepradinol, flufenamic acid, gentisic acid, glucamethacin, glycol salicylate, meclofenamic acid, mefenamic acid, mesalamine, niflumic acid, olsalazine, oxaceprol, S-adenosylmethionine, salicylic acid, salsalate, sulfasalazine, tolfenamic acid and the like.

Anther preferred biologically active compound that can be incorporated into a polymer of the invention is an anti-bacterial, for example, 2-p-sulfanilylanilinoethanol, 4,4'-sulfinyldianiline, 4-sulfanilamidosalicylic acid, acediasulfone, acetosulfone, amikacin, amoxicillin, amphotericin B, ampicillin, apalcillin, apicycline, apramycin, arbekacin, aspoxicillin, azidamfenicol, azithromycin, aztreonam, bacitracin, bambermycin(s), biapenem, brodimoprim, butirosin, capreomycin, carbenicillin, carbomycin, carumonam, cefadroxil, cefamandole, cefatrizine, cefbuperazone, cefclidin, cefdinir, cefditoren, cefepime, cefetamet, cefixime, cefmenoxime, cefminox, cefodizime, cefonicid, cefoperazone, ceforanide, cefotaxime, cefotetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, chloramphenicol, chlortetracycline, ciprofloxacin, clarithromycin, clinafloxacin, clindamycin, clomocycline, colistin, cyclacillin, dapsone, demeclocycline, diathymosulfone, dibekacin, dihydrostreptomycin, dirithromycin, doxycycline, enoxacin, enviomycin, epicillin, erythromycin, flomoxef, fortimicin(s), gentamicin(s), glucosulfone solasulfone , gramicidin S, gramicidin(s), grepafloxacin, guamecycline, hetacillin, imipenem, isepamicin, josamycin, kanamycin(s), leucomycin(s), lincomycin, lomefloxacin, lucensomycin, lymecycline, meclocycline, meropenem, methacycline, micronomicin, midecamycin(s), minocycline, moxalactam, mupirocin, nadifloxacin, natamycin, neomycin, netilmicin, norfloxacin, oleandomycin, oxytetracycline, p-sulfanilylbenzylamine, panipenem, paromomycin, pazufloxacin, penicillin N, pipacycline, pipemidic acid, polymyxin, primycin, quinacillin, ribostamycin, rifamide, rifampin, rifamycin SV, rifapentine, rifaximin, ristocetin, ritipenem, rokitamycin, rolitetracycline, rosaramycin, roxithromycin, salazosulfadimidine, sancycline, sisomicin, sparfloxacin, spectinomycin, spiramycin, streptomycin, succisulfone, sulfachrysoidine, sulfaloxic acid, sulfamidochrysoidine, sulfanilic acid, sulfoxone, teicoplanin, temafloxacin, temocillin, tetracycline, tetroxoprim, thiamphenicol, thiazolsulfone, thiostrepton, ticarcillin, tigemonam, tobramycin, tosufloxacin, trimethoprim, trospectomycin, trovafloxacin, tuberactinomycin, vancomycin and the like.

Anther preferred biologically active compound that can be incorporated into a polymer of the invention is an anti-fungal, for example, azaserine, candicidin(s), chlorphenesin, dermostatin(s), filipin, fungichromin, mepartricin, nystatin, oligomycin(s), perimycin A, tubercidin and the like.

Anther preferred biologically active compound that can be incorporated into a polymer of the invention is an anti-cancer (e.g., carcinomas, sarcomas, leukemias and cancers derived from cells of the nervous system), including anti-neoplastic, for example, 6-azauridine, 6-diazo-5-oxo-L-norleucine, 6-mercaptopurine, aclacinomycin(s), ancitabine, anthramycin, azacitadine, azaserine, bleomycin(s), capecitabine, carubicin, carzinophillin A, chlorozotocin, chromomycin(s), cladribine, cytarabine, daunorubicin, denopterin, docetaxel, doxifluridine, doxorubicin, edatrexate, eflomithine, elliptinium, enocitabine, epirubicin, etoposide, floxuridine, fludarabine, gemcitabine, idarubicin, mannomustine, melphalan, menogaril, methotrexate, mitobronitol, mitolactol, mitomycin C, mitoxantrone, mopidamol, mycophenolic acid, nogalamycin, olivomycin(s), paclitaxel, pentostatin, peplomycin, pirarubicin, piritrexim, plicamycin, podophyllinic acid 2-ethylhydrazine, prednimustine, procarbazine, pteropterin, puromycin, ranimustine, streptonigrin, streptozocin, teniposide, thiamiprine, thioguanine, Tomudex® (N-[[5-[[(1,4-Dihydro-2-methyl-4-oxo-6-quinazolinyl)methyl]methylamino]-2-thienyl]carbonyl]-L-glutamic acid), toptecan, trimetrexate, tubercidin, ubenimex, vinblastine, vindesine, vinorelbine, zorubicin and the like.

Anther preferred biologically active compound that can be incorporated into a polymer of the invention is an anti-thrombotic, for example, argatroban, coumetarol, dicoumarol, ethyl biscoumacetate, ethylidene dicoumarol, iloprost, lamifiban, taprostene, tioclomarol, tirofiban and the like.

Anther preferred biologically active compound that can be incorporated into a polymer of the invention is an immunosuppressive, for example, 6-mercaptopurine, amiprilose, bucillamine, gusperimus, mycophenolic acid, procodazole, romurtide, sirolimus (rapamycin), tacrolimus, ubenimex and the like.

Anther preferred biologically active compound that can be incorporated into a polymer of the invention is a general or local anesthetic, for example, butethamine, fenalcomine, hydroxytetracaine, naepaine, orthocaine, piridocaine, salicyl alcohol and the like.

A specific value for L is a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or (—NR—), and wherein the chain is optionally substituted on carbon with one or more (e.g. 1, 2, 3, or 4) substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy.

Another specific value for L is a divalent, branched or unbranched, saturated or unsaturated, hydrocarbon chain, having from 1 to 25 carbon atoms, wherein the chain is optionally substituted on carbon with one or more (e.g. 1, 2, 3, or 4) substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy.

Another specific value for L is an amino acid.

Another specific value for L is a peptide Another specific value for L is a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or (—NR—).

A more specific value for L is a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—) or (—NR—), and wherein the chain is optionally substituted on carbon with one or more (e.g. 1, 2, 3, or 4) substituents selected from the group consisting of $(C_1-C_6)$ alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy.

Another more specific value for L is a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—) or (—NR—).

Another more specific value for L is a divalent, branched or unbranched, saturated or unsaturated, hydrocarbon chain, having from 3 to 15 carbon atoms.

Another more specific value for L is a divalent, branched or unbranched, hydrocarbon chain, having from 3 to 15 carbon atoms.

A preferred value for L is a divalent, branched or unbranched, hydrocarbon chain, having from 6 to 10 carbon atoms.

A more preferred value for L is a divalent hydrocarbon chain having 7, 8, or 9 carbon atoms.

A most preferred value for L is a divalent hydrocarbon chain having 8 carbon atoms.

A specific polymer of the invention comprises one or more units of formula (I):

$$—R_1\text{-A-L-A-} \quad (I)$$

wherein $R_1$ is group that will provide a biologically active compound upon hydrolysis of the polymer; each A is independently an amide linkage, a thioester linkage, or an ester linkage; and L is a linking group.

Another specific polymer of the invention is a polymer which comprises one or more units of formula (II) in the backbone:

$$—R_2\text{-A-L-A-}R_3\text{-A-L-A-} \quad (II)$$

wherein: $R_2$ and $R_3$ are each independently a group that will yield a biologically active compound upon hydrolysis of the polymer; each A is independently an amide, thioester, or ester linkage; and each L is independently a linking group. Such a polymer, wherein $R_2$ and $R_3$ are groups that will yield differing biologically active compounds upon hydrolysis of the polymer, are particularly useful for the administration of a combination of two therapeutic agents to an animal.

A preferred group of polyesters and polyamides includes polymers that are comprised of compounds containing at least two free alcohol or phenol groups or two at least two free amine groups available for reactions which co-polymerize with carboxylic acid groups or bis(acyl) chlorides.

Formulations

The polymers of the invention can be formulated as pharmaceutical compositions and administered to a mammalian host, such as a human patient in a variety of forms adapted to the chosen route of administration, i.e., orally rectally, or parenterally, by intravenous, intramuscular, intraperitoneal, intraspinal, intracranial, topical or subcutaneous routes. For some routes of administration, the polymer can conveniently be formulated as micronized particles.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations preferably contain at least 0.1% of polymer by weight. The percentage of the compositions and preparations may, of course, be varied and may conveniently be between about 2 to about 80% of the weight and preferably 2 to about 60% of a given unit dosage form. The amount of polymer in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The polymer may also be administered intravenously, intraspinally, intracranially, or intraperitoneally by infusion or injection. Solutions of the polymer can be prepared a suitable solvent such as an alcohol, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile solutions or dispersions or sterile powders comprising the polymer containing the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the polymer in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the present polymers can be applied in pure form. However, it will generally be desirable to administer them as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Dosages

Useful dosages of the polymers can be determined by comparing their in vitro activity, and in vivo activity of the therapeutic agent in animal models. Methods for the extrapolation of effective dosages in mice, and other animals, to humans are known to the art; for example, see U.S. Pat. No. 4,938,949. Additionally, useful dosages can be determined by measuring the rate of hydrolysis for a given polymer under various physiological conditions. The amount of a polymer required for use in treatment will vary not only with the particular polymer selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Combination Therapies

The polymers of the invention are also useful for administering a combination of therapeutic agents to an animal. Such a combination therapy can be carried out in the following ways: 1) a second therapeutic agent can be dispersed within the polymer matrix of a polymer of the invention, and can be released upon degradation of the polymer; 2) a second therapeutic agent can be appended to a polymer of the invention (i.e. not in the backbone of the polymer) with bonds that hydrolyze to release the second therapeutic agent under physiological conditions; 3) the polymer of the invention can incorporate two therapeutic agents into the polymer backbone (e.g. a polymer comprising one or more units of formula (II)) or 4) two polymers of the invention, each with a different therapeutic agent can be administered together (or within a short period of time).

Thus, the invention also provides a pharmaceutical composition comprising a polymer of the invention and a second therapeutic agent that is dispersed within the polymer matrix of a polymer of the invention. The invention also provides a pharmaceutical composition comprising a polymer of the invention having a second therapeutic agent appended to the polymer (e.g. with bonds that will hydrolyze to release the second therapeutic agent under physiological conditions).

The polymers of the invention can also be administered in combination with other therapeutic agents that are effective to treat a given condition to provide a combination therapy. Thus, the invention also provides a method for treating a disease in a mammal comprising administering an effective amount of a combination of a polymer of the invention and another therapeutic agent. The invention also provides a pharmaceutical composition comprising a polymer of the invention, another therapeutic agent, and a pharmaceutically acceptable carrier.

Preferred drug combinations for incorporation into the polymers or the compositions of the invention include the following: amoxicillin/clavulanic acid; and imipenem/cilastatin.

Preparation of Polymers of the Invention

Processes for preparing polymers of the invention are provided as further embodiments of the invention and are illustrated by the following procedures in which the meanings of the generic radicals are as given above unless otherwise qualified.

For example, a polymer of the invention can be prepared, as illustrated in Scheme I, from a biologically active compound of formula ($X_1$—$R_1$—$X_2$) and a linker precursor of formula $Z_1$-L-$Z_2$, wherein $X_1$, $X_2$, $Z_1$, and $Z_2$ are selected from the values in the table below.

Scheme I

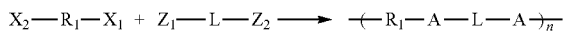

(Ia)

The biologically active compound and the linker precursor can be polymerized using well known synthetic techniques (e.g. by condensation) to provide a polymer of the invention (Ia) wherein each A is independently an ester linkage, a thioester linkage, or an amide linkage.

Depending on the reactive functional group ($X_1$ or $X_2$) of the biologically active compound, a corresponding functional group ($Z_1$ or $Z_2$) can be selected from the following table, to provide an ester linkage, thioester linkage, or amide linkage in the polymer backbone.

| Functional Group On Biologically active compound ($X_1$ or $X_2$) | Functional Group On Linker Precursor ($Z_1$ or $Z_2$) | Resulting Linkage In Polymer |
|---|---|---|
| —COOH | —OH | Ester |
| —COOH | —NHR | Amide |
| —COOH | —SH | Thioester |
| —OH | —COOH | Ester |
| —SH | —COOH | Thioester |
| —NHR | —COOH | Amide |
| —SO$_3$H | —OH | Sulfate Ester |
| —OH | —SO$_3$H | Sulfate Ester |

As will be clear to one skilled in the art, suitable protecting groups can be used during the reaction illustrated in Scheme I (and in the reactions illustrated in Schemes II-XV below). For example, other functional groups present in the biologically active compound or the linker precursor can be protected during polymerization, and the protecting groups can subsequently be removed to provide the polymer of the invention. Suitable protecting groups and methods for their incorporation and removal are well known in the art (see for example Greene, T. W.; Wutz, P. G. M. "Protecting Groups In Organic Synthesis" second edition, 1991, New York, John Wiley & sons, Inc.).

Additionally, when a carboxylic acid is reacted with a hydroxy group, a mercapto group, or an amine group to provide an ester linkage, thioester linkage, or an amide linkage, the carboxylic acid can be activated prior to the reaction, for example, by formation of the corresponding acid chloride.

Numerous methods for activating carboxylic acids, and for preparing ester linkages, thioester linkages, and amide linkages, are known in the art (see for example Advanced Organic Chemistry: Reaction Mechanisms and Structure, 4 ed., Jerry March, John Wiley & Sons, pages 419-437 and 1281).

A polyester of the invention can be formed from a biologically active compound of formula (HO—$R_1$—OH) and from a linker precursor of formula HOOC-L-COOH as illustrated in Scheme II.

SCHEME II

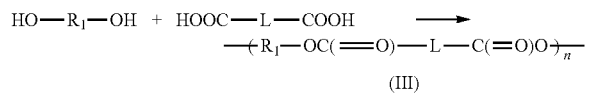

(III)

Reaction of the hydroxy groups of the biologically active compound with the carboxylic acids of the linker precursor provides a polymer of formula (III), which is a polymer of the invention.

A preferred biologically active dihydroxy compound that can be used to prepare a polyester of the invention is: amikacin; amphotericin B; apicycline; apramycin; arbekacin; azidamfenicol; bambermycin(s); butirosin, carbomycin; cefpiramide; chloramphenicol; chlortetracycline; clindamycin; clomocycline; demeclocycline; diathymosulfone; dibekacin; dihydrostreptomycin; dirithromycin; doxycycline; erythromycin; fortimicin(s); gentamicin(s); glucosulfone solasulfone; guamecycline; isepamicin; josamycin; kanamycin(s); leucomycin(s); lincomycin; lucensomycin; lymecycline; meclocycline; methacycline; micronomicin; midecamycin(s); minocycline; mupirocin; natamycin; neomycin; netilmicin; oleandomycin; oxytetracycline; paromomycin; pipacycline; podophyllinic acid 2-ethylhydrazine; primycin; ribostamycin; rifamide; rifampin; rifamycin SV; rifapentine; rifaximin; ristocetin; rokitamycin; rolitetracycline; rosaramycin; roxithromycin; sancycline; sisomicin; spectinomycin; spiramycin; streptomycin; teicoplanin; tetracycline; thiamphenicol; thiostrepton; tobramycin; trospectomycin; tuberactinomycin; vancomycin; candicidin(s); chlorphenesin; dermostatin(s); filipin; fungichromin; mepartricin; nystatin; oligomycin(s); perimycin A; tubercidin; 6-azauridine; aclacinomycin(s); ancitabine; anthramycin; azacitadine; bleomycin(s); carubicin; carzinophillin A; chlorozotocin; chromomycin(s); doxifluridine; enocitabine; epirubicin; gemcitabine; mannomustine; menogaril; atorvastatin; pravastatin; clarithromycin; leuprolide; paclitaxel; mitobronitol; mitolactol; mopidamol; nogalamycin; olivomycin(s); peplomycin; pirarubicin; prednimustine; puromycin; ranimustine; tubercidin; vindesine; zorubicin; coumetarol; dicoumarol; ethyl biscoumacetate; ethylidene dicoumarol; iloprost; taprostene; tioclomarol; amiprilose; romurtide; sirolimus (rapamycin); tacrolimus; salicyl alcohol; bromosaligenin; ditazol; fepradinol; gentisic acid; glucamethacin; olsalazine; S-adenosylmethionine; azithromycin; salmeterol; budesonide; albuterol; indinavir; fluvastatin; streptozocin; doxorubicin; daunorubicin; plicamycin; idarubicin; pentostatin; mitoxantrone; cytarabine; fludarabine phosphate; floxuridine; cladribine; capecitabine; docetaxel; etoposide; topotecan; vinblastine; or teniposide.

A polyamide of the invention can be prepared using a procedure similar to that illustrated in Scheme II by replacing the biologically active dihydroxy compound in Scheme II with a suitable biologically active diamino compound. A preferred biologically active diamino compound that can be used to prepare a polymer of the invention is: 2-p-sulfanilyanilinoethanol; 4,4'-sulfinyldianiline; acediasulfone; acetosulfone; amikacin; apramycin; arbekacin; bacitracin; brodimorprim; butirosin; colistin; capreomycin; dapsone; dibekacin; enviomycin; gramicidin S; polymyxin; teicoplanin; fortimicin(s); gentamicin(s); glucosulfone solasulfone; grepafloxacin; imipenem; isepamicin; kanamycin(s); lymecycline; micronomicin; neomycin; netilmicin; p-sulfanilylbenzylamine; paromomycin; ribostamycin; ristocetin; sisomicin; sparfloxacin; spectinomycin; sulfachrysoidine; sulfamidochrysoidine; sulfoxone; tetroxoprim; thiazolsulfone; tobramycin; trimethoprim; edatrexate; eflomithine; mannomustine; mitoxantrone; peplomycin; piritrexim; procarbazine; pteropterin; trimetrexate; gusperimus; butethamine; naepaine; piridocaine; trospectomycin; tuberactinomycin; vancomycin; candicidin(s); mepartricin; perimycin A; ranitidine; famotidine; metformin; nizatidine; carboplatin; lisinopril; methotrexate; mitomycin bleomycin(s) or thioguanine.

A polythioester of the invention can be prepared using a procedure similar to that illustrated in Scheme II by replacing the biologically active dihydroxy compound in Scheme II with a suitable biologically active dimercapto compound.

A polysulfate ester of the invention can be formed by replacing the dicarboxylic acid linker compound with a disulfo acid compound A polyester/polyamide of the invention can be formed from a biologically active compound of formula (HRN—$R_1$—OH) and from a linker precursor of formula HOOC-L-COOH as illustrated in Scheme III.

SCHEME III

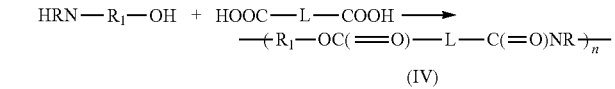

(IV)

Reaction of the hydroxy group and the amino group of the biologically active compound with the carboxylic acids of the linker precursor provides a polymer of formula (IV), which is a polymer of the invention.

A preferred biologically active hydroxy/amino compound that can be used to prepare a polyester/polyamide of the invention is: 2-p-sulfanilyanilinoethanol; 4-sulfanilamidosalicylic acid; amikacin; amphotericin B; apramycin; arbekacin; aspoxicillin; butirosin; capreomycin; cefadroxil; cefatrizine; cefdinir; cefprozil; dibekacin; dihydrostreptomycin; dirithromycin; enviomycin; gramicidin(s); teicoplanin; fortimicin(s); gentamicin(s); glucosulfone solasulfone; isepamicin; kanamycin(s); lucensomycin; lymecycline; meropenem; micronomicin; natamycin; neomycin; netilmicin; paromomycin; ribostamycin; ristocetin; sisomicin; spectinomycin; streptomycin; thiostrepton; tobramycin; trospectomycin; tuberactinomycin; vancomycin; candicidin(s); mepartricin; nystatin; perimycin A; tubercidin; anthramycin; azacitadine; bleomycin(s); carubicin; carzinophillin A; cytarabine; denopterin; elliptinium; epirubicin; gemcitabine; mannomustine; peplomycin; pirarubicin; pteropterin; puromycin; streptonigrin; tubercidin; ubenimex; vindesine; zorubicin; gusperimus; ubenimex; fenalcomine; hydroxytetracaine; orthocaine; 3-amino-4-hydroxybutyric acid; etofenamate; fepradinol; mesalamine; S-adenosylmethionine; leuprolide; acyclovir; paclitaxel; lamivudine; albuterol; indinavir; alendronate; zidovudine; metoprolol; amoxicillin;

salmeterol; imipenem; doxorubicin; daunorubicin; idarubicin; pentostatin; mitoxantrone; fludarabine phosphate; floxuridine; cladribine; vinorelbine; vincristine; or vinblastine.

A polythioester/polyamide of the invention can be prepared using a procedure similar to that illustrated in Scheme II by replacing the hydroxy/amino biologically active compound in Scheme II with a suitable mercapto/amino biologically active compound.

A polyamide of the invention can be formed from a biologically active compound of formula (HOOC—$R_1$—COOH) and from a linker precursor of formula HRN-L-NRH as illustrated in Scheme IV.

SCHEME IV

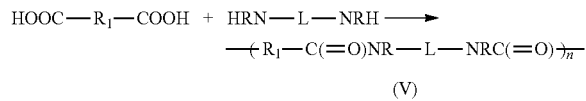

Reaction of the carboxylic acid groups of the biologically active compound with the amino groups of the linker precursor provides a polymer of formula (V), which is a polymer of the invention.

A preferred biologically active dicarboxylic acid compound that can be used to prepare a polyamide of the invention is: bambermycin(s); carbenicillin; carzinophillin A; cefixime; cefminox; cefpimizole; cefodizime; cefonicid; ceforanide; cefotetan; ceftibuten; cephalosporin C; denopterin; edatrexate; moxalactam; olsalazine; penicillin N; quinacillin; temocillin; ticarcillin; Tomudex® (N-[[5-[[(1,4-Dihydro-2-methyl-4-oxo-6-quinazolinyl)methyl]methylamino]-2-thienyl]carbonyl]-L-glutamic acid); lisinopril; cilastatin; ceftazidime; or methotrexate.

A polyester of the invention can be prepared using a procedure similar to that illustrated in Scheme IV by replacing the diamino linker precursor with a dihydroxy linker precursor. Similarly, a polyester/polyamide of the invention can be prepared using a procedure similar to that illustrated in Scheme IV by replacing the diamino linker precursor with an hydroxy/amino linker precursor; and a polythioester/polyamide of the invention can be prepared using a procedure similar to that illustrated in Scheme IV by replacing the diamino linker precursor with an mercapto/amino linker precursor.

A polyester of the invention can be formed from a biologically active compound of formula (HO—$R_1$—COOH) and from a linker precursor of formula HO-L-COOH as illustrated in Scheme V.

SCHEME V

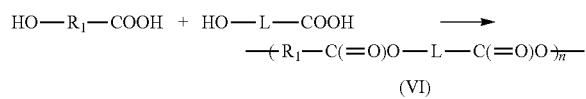

Reaction of the hydroxy group and the carboxylic acid of the biologically active compound, with the carboxylic acid and the hydroxy group of the linker precursor provides a polymer of formula (VI), which is a polymer of the invention.

A preferred biologically active hydroxy/carboxylic acid compound that can be used to prepare a polymer of the invention is: 4-sulfanilamidosalicylic acid; amphotericin B; apalcillin; apicycline; aspoxicillin; bambermycin(s); biapenem; cefadroxil; cefamandole; cefatrizine; cefbuperazone; cefdinir; cefonicid; cefoperazone; cefpiramide; cefprozil; enviomycin; teicoplanin; flomoxef; glycol salicylate; lucensomycin; lymecycline; meropenem; moxalactam; mupirocin; nadifloxacin; natamycin; panipenem; podophyllinic acid 2-ethylhydrazine; ritipenem; salazosulfadimidine; sulfaloxic acid; vancomycin; 3-amino-4-hydroxybutyric acid; candicidin(s); carzinophillin A; denopterin; diflunisal; fendosal; gentisic acid; iloprost; lamifiban; mesalamine; nystatin; olsalazine; oxaceprol; pteropterin; romurtide; salicylic acid; salsalate; streptonigrin; sulfasalazine; taprostene; ubenimex; amoxicillin; pravastatin; imipenem; mycophenolic acid; or fluvastatin.

A polyester/polyamide of the invention can be prepared using a procedure similar to that illustrated in Scheme V by replacing biologically active hydroxy/carboxylic compound with a biologically active amino/carboxylic acid compound. A preferred biologically active amino/carboxylic acid compound that can be used to prepare a polymer of the invention is: 3-amino-4-hydroxybutyric acid; 4-sulfanilamidosalicylic acid; 6-diazo-5-oxo-L-norleucine; aceclofenac; acediasulfone; alminoprofen; amfenac; amphotericin B; ampicillin; argatroban; aspoxicillin; azaserine; aztreonam; bromfenac; bumadizon; candicidin(s); carprofen; carumonam; carzinophillin A; cefadroxil; cefatrizine; cefclidin; cefdinir; cefditoren; cefepime; cefetamet; cefixime; cefmenoxime; cefminox; cefodizime; ceforanide; cefotaxime; cefotiam; cefozopran; cefpirome; cefprozil; cefroxadine; ceftazidime; cefteram; ceftibuten; ceftriaxone; cefuzonam; cephalexin; cephaloglycin; cephalosporin C; cephradine; clinafloxacin; cyclacillin; denopterin; edatrexate; eflomithine; enfenamic acid; enoxacin; epicillin; etodolac; enviomycin; teicoplanin; flufenamic acid; grepafloxacin, hetacillin; imipenem; lomefloxacin; lucensomycin; lymecycline; meclofenamic acid; mefenamic acid; meropenem; mesalamine; natamycin; niflumic acid; norfloxacin; nystatin; pazufloxacin; penicillin N; pipemidic acid; procodazole; pteropterin; S-adenosylmethionine; sparfloxacin; streptonigrin; succisulfone; sulfachrysoidine; temafloxacin; tigemonam; tirofiban; tolfenamic acid; tosufloxacin; trovafloxacin; ubenimex; vancomycin; enalapril; amoxicillin; ciprofloxacin; diclofenac; lisinopril; ceftriaxone; cilastatin; benazepril; cefaclor; ceftazidime; quinapril; melphalan; or methotrexate.

A polythioester/polyester of the invention can be prepared using a procedure similar to that illustrated in Scheme V by replacing biologically active hydroxy/carboxylic compound with a biologically active mercapto/carboxylic acid compound. A preferred biologically active mercapto/carboxylic acid compound that can be used to prepare a polymer of the invention is bucillamine or captopril.

A polysulfonamide of the invention can be prepared using a procedure similar that illustrated in Scheme V by replacing the biologically active hydroxy/carboxylic compound with a biologically active amine/sulfo acid compound. A preferred biologically active amine/sulfo acid compound that can be used to prepare a polymer of the invention is: sulfanilic acid or sulfoxone.

In the polymers of formulae (I, and III-VI) illustrated in Schemes I-V above, $R_1$, A, L, and R can have any of the values, specific values, or preferred values described herein.

The co-polymerization of morphine with a diacid chloride to provide a polyester of the invention is depicted in Scheme VI.

Scheme VI

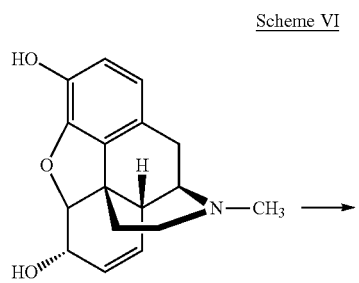

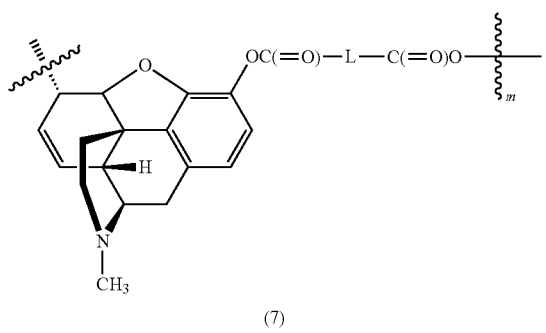

(7)

In the reaction illustrated in Scheme VI, the linking group L is preferably —(CH$_2$)$_x$—, and more preferably, L is —(CH$_2$)$_8$—. A polymer of formula (7) wherein L has any of the values, specific values, or preferred values described herein is a preferred polymer of the invention. For a polymer of formula (7), m is an integer that is greater than or equal to 2.

The co-polymerization of dopamine with bis(acyl) chloride to provide a polyester of the invention is depicted in Scheme VII.

Scheme VII

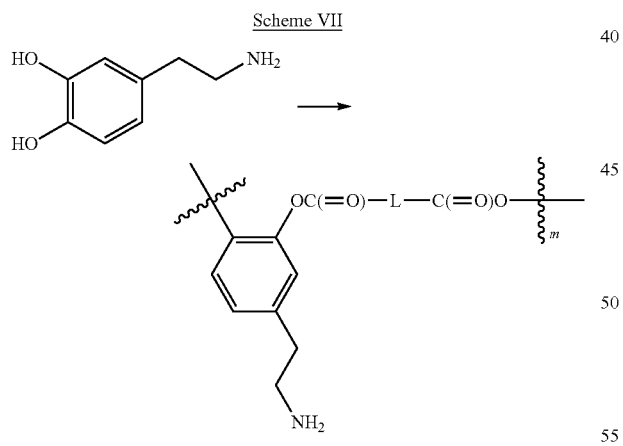

(8)

In the reaction illustrated in Scheme VII, the linking group L is preferably —(CH$_2$)$_x$—, and more preferably, L is —(CH$_2$)$_8$—. A polymer of formula (8) wherein L has any of the values, specific values, or preferred values described herein is a preferred polymer of the invention. For a polymer of formula (8), m is an integer that is greater than or equal to 2. Prior to the polymerization illustrated in Scheme VII, the amino group of dopamine can be protected with a suitable protecting group, which can subsequently be removed, to provide the polymer of the invention.

It should be noted that dopamine can also be incorporated into a polyester/polyamide of the invention by reacting the amino group and either hydroxy group of dopamine with a compound of formula HOOC-L-COOH, or an activated derivative thereof to provide a compound of formula (21) or (22):

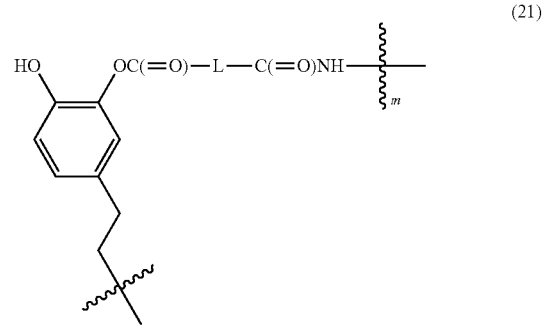

(21)

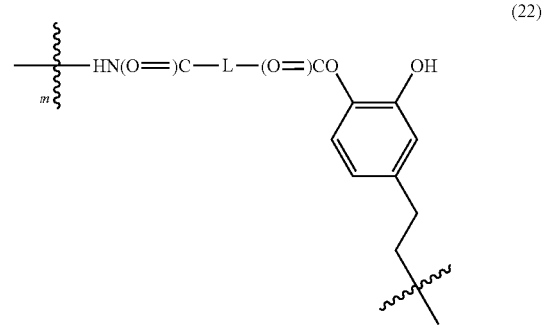

(22)

Prior to the polymerization, the hydroxy group which will not be polymerized can be protected with a suitable protecting group, which can subsequently be removed to provide the polymer of the invention.

The co-polymerization of acriflavine to provide a polyamide of the invention is depicted in Scheme VIII.

Scheme VIII

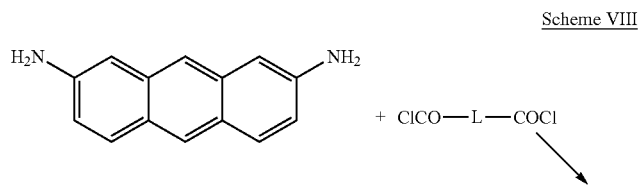

+ ClCO—L—COCl

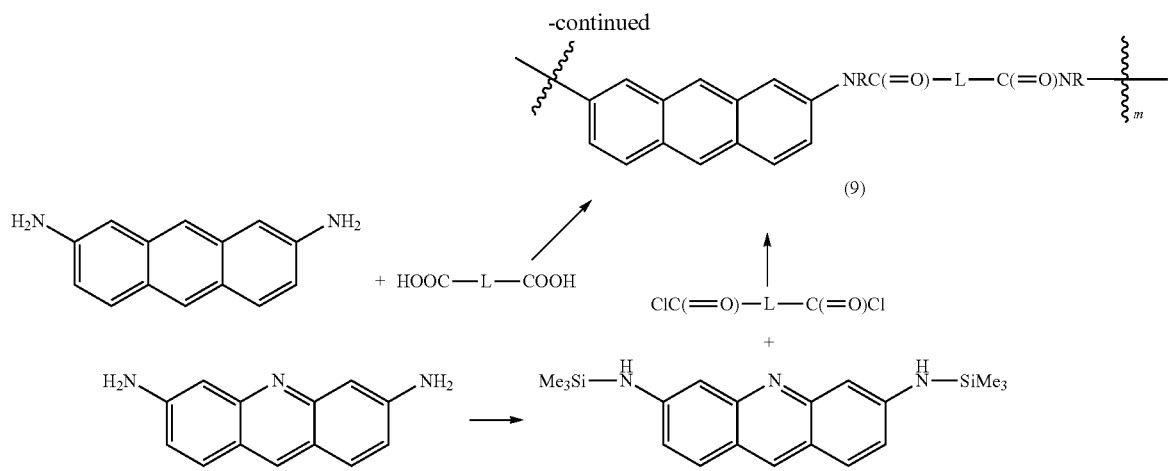

The diamino groups of acriflavine are copolymerized in solution (preferably high-boiling point organic solvent such as dimethylformamide) with an activated dicarboxylic acid (e.g. sebacoyl chloride). The polyamide is isolated by methods well known in the art. Alternatively, the amino groups can be reacted with a dicarboxylic acid by employing high temperatures (e.g. in the melting range), or a coupling agent. This process of making polyamides is also well known to those skilled in the art. In yet another embodiment, the diamino groups can be activated in the presence of hexamethylsilazine to form silylated amines. The silylated amines lo can then be allowed to react with an activated dicarboxylic acid (e.g. sebacyl chloride) to provide a polymer of the invention.

In the reaction illustrated in Scheme VIII, the linking group L is preferably —$(CH_2)_x$—, and more preferably, L is —$(CH_2)_8$—. A polymer of formula (9) wherein L has any of the values, specific values, or preferred values described herein is a preferred polymer of the invention. For a polymer of formula (9), m is an integer that is greater than or equal to 2.

The preparation of a polymer of the invention comprising methotrexate is illustrated in Scheme IX.

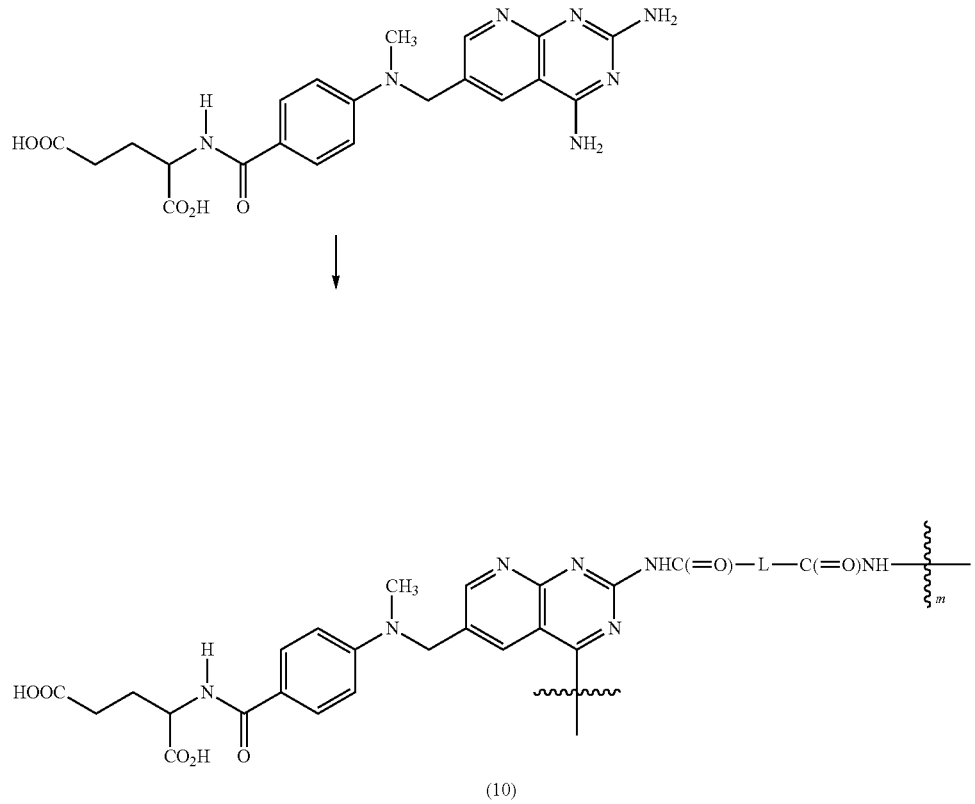

In the reaction illustrated in Scheme IX, the linking group L is preferably —(CH$_2$)$_x$—, and more preferably, L is —(CH$_2$)$_8$—. A polymer of formula (10) wherein L has any of the values, specific values, or preferred values described herein is a preferred polymer of the invention. For a polymer of formula (10), m is an integer that is greater than or equal to 2. Prior to the polymerization illustrated in Scheme IX, the carboxylic acids of methotrexate can be protected with suitable protecting groups, which can subsequently be removed, to provide the polymer of the invention.

It will be appreciated by one skilled in the art that a polymer of the invention of the following formula (20):

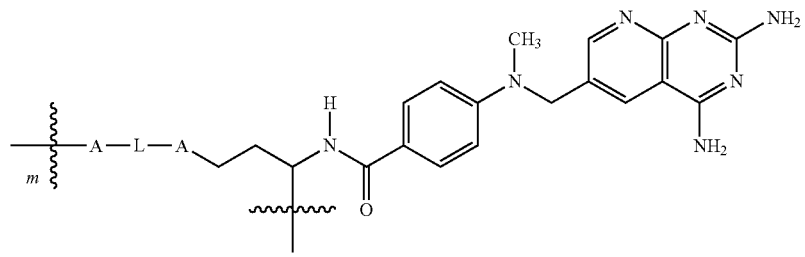

wherein each A is independently an ester linkage, a thioester linkage, or an amide linkage can be prepared as illustrated in Scheme X by selecting a linker precursor with the appropriate functionality. For a compound of formula (20) the linking group L is preferably —(CH$_2$)$_x$—, and more preferably, L is —(CH$_2$)$_8$—. A polymer of formula (20) wherein L and each A has any of the values, specific values, or preferred values described herein is a preferred polymer of the invention. For a polymer of formula (20), m is an integer that is greater than or equal to 2.

The preparation of another polymer of the invention comprising methotrexate is illustrated in Scheme X.

Scheme X

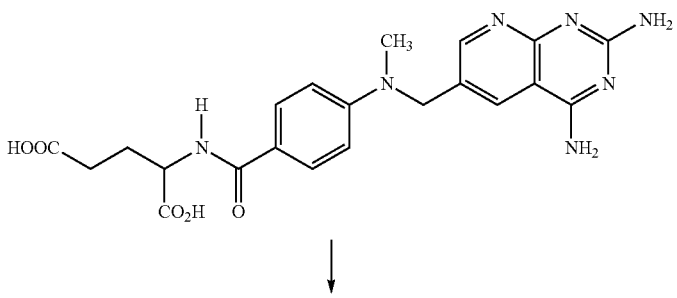

↓

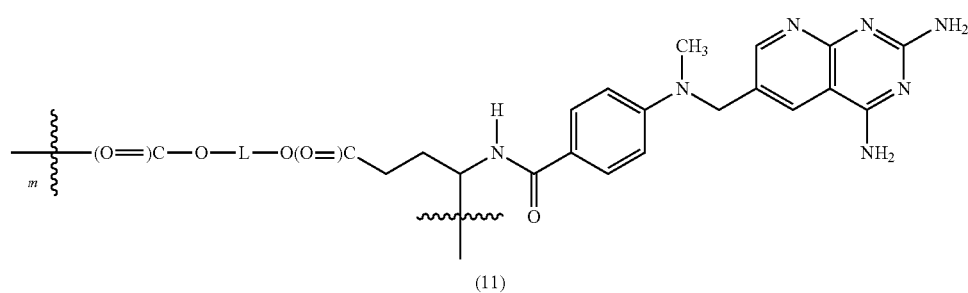

(11)

In the reaction illustrated in Scheme X, the linking group L is preferably —(CH$_2$)$_x$—, and more preferably, L is —(CH$_2$)$_8$—. A polymer of formula (11) wherein L has any of the values, specific values, or preferred values described herein is a preferred polymer of the invention. For a polymer of formula (11), m is an integer that is greater than or equal to 2. Prior to the polymerization illustrated in Scheme X, the amino groups of methotrexate can be protected with suitable protecting groups, which can subsequently be removed, to provide the polymer of the invention.

The preparation of another polymer of the invention comprising methotrexate is illustrated in Scheme XI.

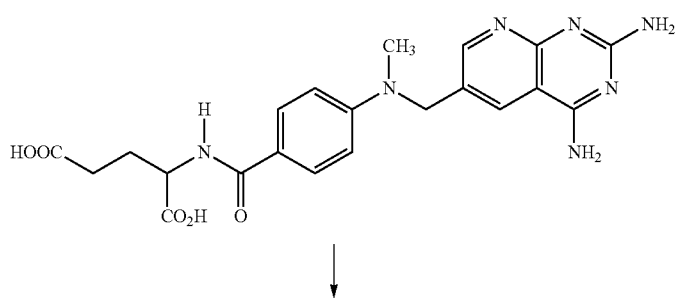

Scheme XI (12)

In the reaction illustrated in Scheme XI, the linking group L is preferably —(CH$_2$)$_x$—, and more preferably, L is —(CH$_2$)$_8$—. A polymer of formula (12) wherein L has any of the values, specific values, or preferred values described herein is a preferred polymer of the invention. For a polymer of formula (12), m is an integer lo that is greater than or equal to 2. Prior to the polymerization illustrated in Scheme XI, the carboxylic acid and amino group of methotrexate that are not reacted to form the polymer can be protected with suitable protecting groups, which can subsequently be removed, to provide the polymer of the invention.

A polymer of the invention that comprises methotrexate is particularly useful for treating psoriasis, inflammatory bowel disease, skin cancer, or brain tumors. Such a polymer is also particularly useful as an anti-neoplastic agent anti-infective agent, and for local administration of an anti-tumor agent following a lumpectomy or mastectomy.

The preparation of a polymer of the invention comprising doxorubicin is illustrated in Scheme XII.

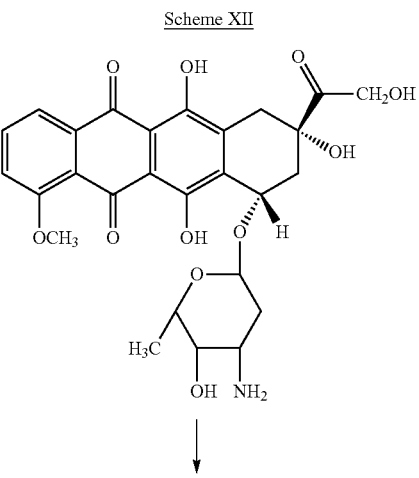

Scheme XII

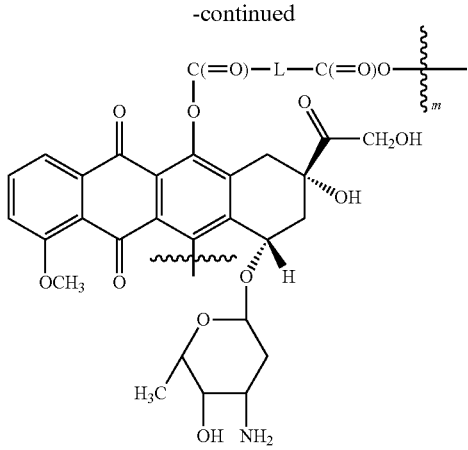

(13)

In the reaction illustrated in Scheme XII, the linking group L is preferably —(CH$_2$)$_x$—, and more preferably, L is —(CH$_2$)$_8$—. A polymer of formula (13) wherein L has any of the values, specific values, or preferred values described herein is a preferred polymer of the invention. For a polymer of formula (13), m is an integer that is greater than or equal to 2. Prior to the polymerization illustrated in Scheme XII, the functional groups of doxorubicin that are not reacted to form the polymer can be protected with suitable protecting groups, which can subsequently be removed, to provide the polymer of the invention.

A polymer of the invention that comprises doxorubicin is particularly useful for local administration as an anti-tumor (e.g. brain tumor) agent or anti-neoplastic agent.

The preparation of a polymer of the invention comprising daunorubicin is illustrated in Scheme XIII.

Scheme XIII

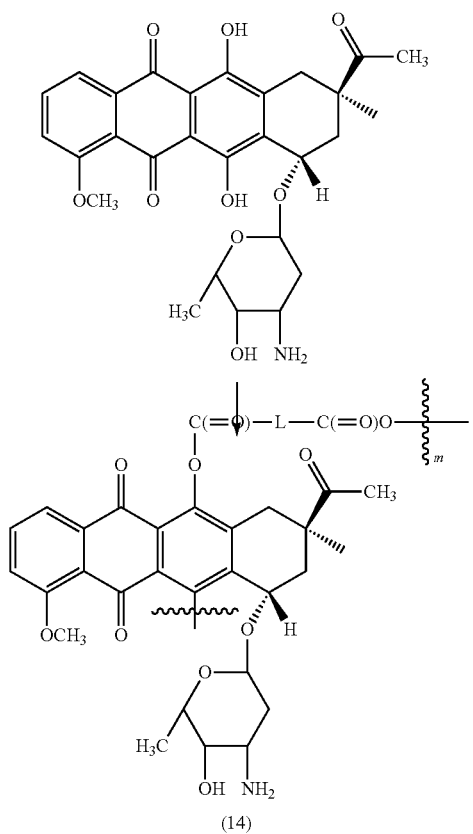

(14)

In the reaction illustrated in Scheme XIII, the linking group L is preferably —(CH$_2$)$_x$—, and more preferably, L is —(CH$_2$)$_8$—. A polymer of formula (14) wherein L has any of the values, specific values, or preferred values described herein is a preferred polymer of the invention. For a polymer of formula (14), m is an integer that is greater than or equal to 2. Prior to the polymerization illustrated in Scheme XIII, the functional groups of daunorubicin that are not reacted to form the polymer can be protected with suitable protecting groups, which can subsequently be removed, to provide the polymer of the invention.

A polymer of the invention that comprises daunorubicin is particularly useful for local administration as an anti-tumor (e.g. brain tumor) agent or an anti-neoplastic agent.

The preparation of a polymer of the invention comprising 5-aminosalicylic acid is illustrated in Scheme XIV.

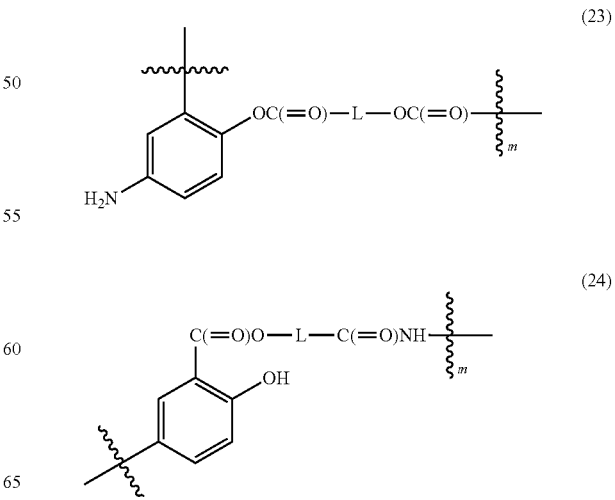

(15)

In the reaction illustrated in Scheme XIV, the linking group L is preferably —(CH$_2$)$_x$—, and more preferably, L is —(CH$_2$)$_8$—. A polymer of formula (15) wherein L has any of the values, specific values, or preferred values described herein is a preferred polymer of the invention. For a polymer of formula (15), m is an integer that is greater than or equal to 2. Prior to the polymerization illustrated in Scheme XIV, the carboxylic acid can be protected with a suitable protecting group, which can subsequently be removed, to provide the polymer of the invention.

5-Aminosalicilic acid can also be incorporated into a polymer of the invention which is a polymer of formula (23) or (24):

(23)

(24)

The preparation of a polymer of the invention comprising mycophenolic acid is illustrated in Scheme XV.

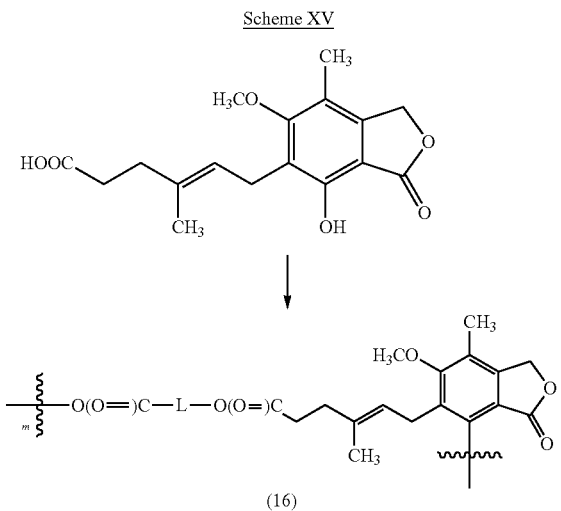

In the reaction illustrated in Scheme XV, the linking group L is preferably —(CH$_2$)$_x$—, and more preferably, L is —(CH$_2$)$_8$—. A polymer of formula (16) wherein L has any of the values, specific values, or preferred values described herein is a preferred polymer of the invention. For a polymer of formula (16), m is an integer that is greater than or equal to 2.

Activity

The ability of a polymer of the invention to produce a given therapeutic effect can be determined using in vitro and in vivo pharmacological models which are well known to the art.

All publications, patents, and patent documents (including the entire contents of U.S. Provisional Patent Application No. 60/220,707, filed 27 Jul. 2000) are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A polymer which comprises one or more units of formula (II) in the backbone:

wherein
R$_2$ and R$_3$ are each independently a group that will yield an anticancer agent upon hydrolysis of the polymer;
each A is independently an amide or ester linkage; and
each L is independently a linking group.

2. The polymer of claim 1 wherein the anticancer agent is selected from 6-azauridine, 6-diazo-5-oxo-L-norleucine, 6-mercaptopurine, aclacinomycin(s), ancitabine, anthramycin, azacitadine, azaserine, bleomycin(s), capecitabine, carubicin, carzinophillin A, chlorozotocin, chromomycin(s), cladribine, cytarabine, daunorubicin, denopterin, docetaxel, doxifluridine, doxorubicin, edatrexate, eflornithine, elliptinium, enocitabine, epirubicin, etoposide, floxuridine, fludarabine, gemcitabine, idarubicin, mannomustine, melphalan, menogaril, methotrexate, mitobronitol, mitolactol, mitomycin C, mitoxantrone, mopidamol, mycophenolic acid, nogalamycin, olivomycin(s), paclitaxel, pentostatin, peplomycin, pirarubicin, piritrexim, plicamycin, podophyllinic acid 2-ethylhydrazine, prednimustine, procarbazine, pteropterin, puromycin, ranimustine, streptonigrin, streptozocin, teniposide, thiamiprine, thioguanine, N-[[5-[[1,4-Dihydro-2-methyl-4-oxo-6-quinazolinyl)methyl]methylamino]-2-thienyl]carbonyl]-L-glutamic acid), toptecan, trimetrexate, tubercidin, ubenimex, vinblastine, vindesine, vinorelbine, and zorubicin.

3. The polymer of claim 1 wherein L is a divalent, branched or unbranched, saturated or unsaturated, hydrocarbon chain, having from 1 to 25 carbon atoms, wherein one or more of the carbon atoms is optionally replaced by (—O—), and wherein the chain is optionally substituted on carbon with one or more substituents selected from the group consisting of (C$_1$-C$_6$) alkoxy, (C$_3$-C$_6$)cycloalkyl, (C$_1$-C$_6$)alkanoyl, (C$_1$-C$_6$)alkanoyloxy, (C$_1$-C$_6$)alkoxycarbonyl, (C$_1$-C$_6$)alkylthio, azido, cyano, nitro, halo, hydroxy, oxo, carboxy, aryl, aryloxy, heteroaryl, and heteroaryloxy.

4. The polymer of claim 1 wherein L is a divalent, branched or unbranched, saturated or unsaturated, hydrocarbon chain, having from 1 to 25 carbon atoms, wherein the chain is optionally substituted on carbon with one or more substituents selected from the group consisting of (C$_1$-C$_6$)alkoxy, (C$_3$-C$_6$)cycloalkyl, (C$_1$-C$_6$)alkanoyl, (C$_1$-C$_6$)alkanoyloxy, (C$_1$-C$_6$)alkoxycarbonyl, (C$_1$-C$_6$)alkylthio, azido, cyano, nitro, halo, hydroxy, oxo, carboxy, aryl, aryloxy, heteroaryl, and heteroaryloxy.

5. The polymer of claim 1 wherein L is a peptide.

6. The polymer of claim 1 wherein L is an amino acid.

7. The polymer of claim 1 wherein L is a divalent, branched or unbranched, saturated or unsaturated, hydrocarbon chain, having from 1 to 25 carbon atoms, wherein one or more of the carbon atoms is optionally replaced by (—O—).

8. The polymer of claim 1 wherein L is a divalent, branched or unbranched, saturated or unsaturated, hydrocarbon chain, having from 3 to 15 carbon atoms, wherein one or more of the carbon atoms is optionally replaced by (—O—), and wherein the chain is optionally substituted on carbon with one or more substituents selected from the group consisting of (C$_1$-C$_6$) alkoxy, (C$_3$-C$_6$)cycloalkyl, (C$_1$-C$_6$)alkanoyl, (C$_1$-C$_6$)alkanoyloxy, (C$_1$-C$_6$)alkoxycarbonyl, (C$_1$-C$_6$)alkylthio, azido, cyano, nitro, halo, hydroxy, oxo, carboxy, aryl, aryloxy, heteroaryl, and heteroaryloxy.

9. The polymer of claim 1 wherein L is a divalent, branched or unbranched, saturated or unsaturated, hydrocarbon chain, having from 3 to 15 carbon atoms, wherein one or more of the carbon atoms is optionally replaced by (—O—).

10. The polymer of claim 1 wherein L is a divalent, branched or unbranched, saturated or unsaturated, hydrocarbon chain, having from 3 to 15 carbon atoms.

11. The polymer of claim 1 where in L is a divalent, branched or unbranched, hydrocarbon chain, having from 3 to 15 carbon atoms.

12. The polymer of claim 1 wherein L is a divalent, branched or unbranched, hydrocarbon chain, having from 6 to 10 carbon atoms.

13. The polymer of claim 1 wherein L is a divalent hydrocarbon chain having 7, 8, or 9 carbon atoms.

14. The polymer of claim 1 wherein L is a divalent hydrocarbon chain having 8 carbon atoms.

15. A pharmaceutical composition comprising a polymer of claim 1 and a pharmaceutically acceptable carrier.

16. A method for producing a polymer as described in claim 1 comprising co-polymerizing an anticancer agent containing at least two alcohol or phenol groups or at least two amine groups with carboxylic acid groups or bis(acyl) chlorides.

17. A method of delivering an anticancer agent to a host comprising administering to the host a polymer of claim 1.

* * * * *